US00PP22107P3

(12) United States Plant Patent
Cavett

(10) Patent No.: US PP22,107 P3
(45) Date of Patent: Sep. 6, 2011

(54) *ZELKOVA* TREE NAMED 'JSC KINGSTHREE'

(50) Latin Name: *Zelkova serrata*
Varietal Denomination: JSC Kingsthree

(76) Inventor: James David Cavett, Estill Springs, TN (US)

( * ) Notice: Subject to any disclaimer, the term of this patent is extended or adjusted under 35 U.S.C. 154(b) by 0 days.

(21) Appl. No.: 12/592,405

(22) Filed: Nov. 24, 2009

(65) Prior Publication Data

US 2011/0126333 P1 May 26, 2011

(51) Int. Cl.
*A01H 5/00* (2006.01)

(52) U.S. Cl. ..... Plt./216

(58) Field of Classification Search ..... Plt./216
See application file for complete search history.

(56) References Cited

OTHER PUBLICATIONS

Burghardt. Japanese *Zelkova* Trees, 2010 retrieved on Nov. 30, 2010. Retrieved from the Internet at <http://www.ehow.com/list_7354806_japanese-zelkova-trees.html> 3 pp.*

* cited by examiner

*Primary Examiner* — June Hwu
(74) *Attorney, Agent, or Firm* — Jason L. Hornkohl; Kornkohl Intellectual Property, Law PLLC

(57) ABSTRACT

A new and distinct *Zelkova serrata* cultivar, named the 'JSC Kingsthree' *Zelkova* is characterized by its weeping branch structure, different fall leaf color, texture and curl of its leaves, and the manner in which sunlight passes through its pubescent petioles when the sun is low on the horizon, which makes the tree look as if it is covered with frost. The inventor is unaware of any other *Zelkova serrata* trees that exhibit any of these characteristics. The 'JSC Kingsthree' *Zelkova* is also characterized by its drought and cold tolerance.

8 Drawing Sheets

Latin name: *Zelkova serrata.*
Varietal denomination: 'JSC KINGSTHREE'.

FIELD OF THE INVENTION

The present invention comprises a new and distinct cultivar of *Zelkova serrata* and is referred to by the cultivar name 'JSC Kingsthree'.

BACKGROUND OF THE INVENTION

This new cultivar of *Zelkova serrata,* the 'JSC Kingsthree' *zelkova,* originated as a single seedling that was discovered by James David Cavett in 2005 in a group of *Zelkova serrata* planted in a field on the nursery of James D. Cavett at 74 S & W Lane, Estill Springs, Tenn. 37330. James D. Cavett grafted four buds from the new cultivar, 'JSC Kingsthree' onto *Zelkova serrata* seedlings in 1-gallon containers at 74 S&W Lane, Estill Springs, Tenn. 37330 in July 2005. Two of the 4 grafted seedlings survived. In February 2007, a second generation of sixty-five grafted seedlings were started from these 2 surviving grafted seedlings. Exactly 63 of the grafted seedlings begun in February 2007 survived and were used to begin a third generation of 250 new grafted seedlings in February 2008. Two-hundred of these 250 new grafted seedlings survived. In February 2009, approximately 500 grafted 'JSC Kingsthree' seedlings were taken and grafted onto *Zelkova serrata* seedlings; approximately 350 emerged and survived. In February 2009, rooted cuttings were also used to grow the new *Zelkova serrata* cultivar. In February 2009, 150 rooted cuttings were taken from the new 'JSC Kingsthree' *Zelkova serrata* cultivars and rooted in sand using indole-3-butyric acid at 74 S&W Lane, Estill Springs, Tenn. 37330, and 100 survived. In June 2009, 1500 additional rooted cuttings were begun, and 1200 survived. In July 2009, 6000 additional rooting cuttings of 'JSC Kingsthree' were begun, and 4500 survived. Over the last four years, all of the grafted seedlings and rooted cuttings of 'JSC Kingsthree' have exhibited several different growing characteristics and patterns than the parent plant *Zelkova serrata* as well as differences in leaf pigmentation, leaf shape (it curls around itself), and leaf texture. Furthermore, the branches of the new 'JSC Kingsthree' cultivars exhibit a weeping growth pattern; whereas, traditional *Zelkova serrata* do not weep. At the end of many branches of the 'JSC Kingsthree', the branch makes a 30 to 60-degree bend at a leaf bud (See FIG. 2). When the leaves first emerge from their apical meristems, they are reddish-brown (RHS #171A [when further referring to the coloring of the specimen, the RHS color designation is derived from The 2005 R.H.S. Mini Colour Chart]). They quickly become light green for 2 to 3 weeks, turning dark green as they mature. The upper side of young leaves (three-week-old leaves) is (RHS #137A); the color of the upper side of the most mature leaves is dark green (RHS #136A). The color of the lower side of the immature leaf is a light green (RHS #141D), but changes in the most mature leaves to a darker green (RHS #144A). During fall, the margin of the leaf becomes reddish-brown (RHS #171A) and the leaf along the main vein changes from a light yellow-brown (RHS # 163B) to a reddish-brown (RHS #171A). From the emergence of the leaves from the bud, both new growth and mature leaves curl along the axis of the main vein that differs from the leaf of the parent plant. Another characteristic of the 'JSC Kingsthree' leaves that differs from the parent plant is that both new growth and mature leaves have a "velvet" texture because of tiny hairs located on the lower and upper epidermis of the leaf. The branches of the 'JSC Kingsthree' cultivar weep unlike the parental *Zelkova serrata.* Also, the terminal end of many branches makes a 90-degree angle at a distal leaf axis (see FIG. 6). James D.

Cavett has been evaluating these grafted seedlings for four years and evaluating the rooted cuttings for one year.

James D. Cavett is solely responsible for finding this new cultivar, known as 'JSC Kingsthree', on his property located at 74 S&W Lane, Estill Springs, Tenn. 37330. All grafted seedlings and rooted cuttings of this cultivar have been done by James D. Cavett at his nursery located at 74 S&W Lane, Estill Springs, Tenn. 37330.

James D. Cavett immediately recognized that the new cultivar 'JSC Kingsthree' exhibited new and distinctive leaf pigmentation, leaf shape (curling around the main leaf vein), leaf sculpturing, leaf texture, branch structure, and growth pattern. The leaves are reddish-brown (see FIG. 3) when they first emerge from the bud and, within the first 3 weeks, the leaf exhibits a light green pigmentation. As the leaf enlarges and matures; however, the leaf pigmentation becomes dark green. The mature leaf is dark green in color. Only the seedlings that have originated from the grafted or rooted seedlings of the newly discovered cultivar, known as 'JSC Kingsthree', exhibit these new characteristics that are distinctively different from the parental *Zelkova serrata* from which it originated as well as differs from all known Japanese *Zelkova* trees by exhibiting its unique leaf curl, branch structure and leaf texture which are not found in any other known species of *Zelkova.* Another difference between the 'JSC Kingsthree' cultivar and the ordinary *Zelkova serrata* is the presence of trichomes all over the upper and lower surfaces of the leaves as well as on the petioles (see FIG. 5). In the *Zelkova serrata,* trichomes are not visibly present. The leaf shape also differs between the 'JSC Kingsthree' and *Zelkova serrata* cultivars in that the leaf of the 'JSC Kingsthree' has a prominent curl along the axis of the main leaf vein (see FIG. 7). There is no such curl present in the regular *Zelkova serrata.* Finally, the branches of the 'JSC Kingsthree' differ in several ways from the parent *Zelkova serrata* plant: first the limbs grow at a 30 to 60-degree angle (see FIGS. 1 and 2), and at the terminal end of some of the limbs, there is a 90-degree bend in the limb (see FIG. 6). Neither of these are characteristics present in *Zelkova serrata.* Over the last 4 years, both the grafted seedlings and rooted cuttings have exhibited this pigmentation, leaf curling, leaf texture, and branch structure as compared to other *Zelkova serrata* trees.

The 'JSC Kingsthree' cultivar has proven to be both drought resistant and very winter hardy. In April 2007, Middle Tennessee (climate Zone 6b, USDA Plant Hardiness Zone Map) experienced an unusually late freeze during which the overnight temperatures dropped into the low 20's F. This was a particularly dangerous and damaging freeze because most of the trees had already budded. The 'JSC Kingsthree' cultivar survived this freeze and continued to produce foliage throughout the spring and summer months. All grafted seedlings and rooted cuttings taken from the plants exhibit the same moderate growth that has been observed for the last 4 growing seasons that the 'JSC Kingsthree' cultivar has been cultivated.

The 'JSC Kingsthree' cultivar can also endure drastic fluctuations in moisture. 'JSC Kingsthree' cultivar has been successfully grown without irrigation after it is moved into the fields during its second season. Each summer since it was grafted in 2004, it has endured the drought that Middle Tennessee has experienced during the months of July and August. Middle Tennessee usually experiences heavy rainfalls during the spring; however, immediately after the late spring 2007 freeze, another unusual meteorological event occurred; Middle Tennessee experienced an early 2-month drought. While many annuals, perennials, shrubs, and trees were severely damaged or killed by the late spring freeze that was followed by a 2-month drought, the 'JSC Kingsthree' cultivar survived and demonstrated itself to be cold and drought tolerant.

The 'JSC Kingsthree' cultivar has been successfully grafted asexually. The proven means of asexual propagation has been rooted softwood cuttings and grafting. In 2005, when the new cultivar was discovered by James D. Cavett, four buds were removed and grafted onto *Zelkova serrata* seedlings planted in a one-gallon container located at 74 S&W Lane, Estill Springs, Tenn. 37330, and two survived. In February 2007, 65 grafted cultivar seedlings were started from the two surviving 'JSC Kingsthree' seedlings that had been grafted 2005, and 63 survived. In February 2008, 200 of 250 grafts taken from the other 'JSC Kingsthree' trees were grafted and survived. In February 2009, 500 grafted seedlings were taken from the 'JSC Kingsthree' trees and grafted onto the *Zelkova serrata* seedlings; approximately 350 survived grafted seedlings survived. In February 2009, 150 rooted cuttings were started and 100 survived. In June 2009, 1500 rooted cuttings were started and 1200 survived. In July 2009, an additional 6000 rooted cuttings were started and 4500 survived. The cultivars (both grafted seedlings and rooted cuttings) have retained all the characteristics of the original selected seedling, the cultivar known as 'JSC Kingsthree'. The 'JSC Kingsthree' cultivar has been successfully grafted through 4 generations of asexual reproduction with a survival rate of 97% during the second year (2007), 80% during the third year (2008), and 70% during the fourth year (2009) for grafted seedlings. The survival rate of the rooted cuttings approximates the survival rate of grafted seedlings. The rooted cuttings that were begun February 2009 had a survival rate of 66%; the June 2009 rootings had a survival rate of 80%, and the July 2009 cuttings had a survival rate of 75%. Every generation of the 'JSC Kingsthree' cultivar that has been asexually propagated has been stable and produced true-to-type plants.

The unique color, shape and texture of the leaves, growth pattern, branching structure and moderate growth (3 to 4 feet per year) of the 'JSC Kingsthree' cultivar make it well suited for a variety of landscaping uses. Furthermore, the 'JSC Kingsthree' cultivar is cold and drought tolerant. The cultivar is a moderate size tree whose leaf pigmentation changes from light green to dark green. For the first three weeks after the leaf emerges from its bud, it is reddish-brown in color; however, as the leaf enlarges, the pigmentation becomes a dark green color, the color of the mature leaf. The dark green color of the leaves of the 'JSC Kingsthree' cultivar will make it a hardier *zelkova* for those who desire an attractive landscaping tree. In the fall the leaves turn from a dark green to a mixture consisting of reds, maroons, and yellow-browns. Some of the leaves of the 'JSC Kingsthree' cultivar also exhibit a pronounced curl along the leaf's main vein, and all leaves exhibit a velvet texture, which differs from the straight, flat leaf of the *Zelkova serrata.* The petiole of the leaf has an extremely large number of trichomes, which in the correct lighting conditions (early morning or late afternoon) cause the tree to appear to be covered with frost. Finally, the limbs follow a different growth pattern than that of the *Zelkova serrata.* The branches "bend" or "droop" at approximately 30 to 60 degrees in the middle of the growing branch, which does not occur in the general *Zelkova serrata.* Continued branch growth after this bend occurs results in the weeping appearance of the tree. There is also a distinct bend near the terminal end of some branches, where the branch growth changes direction and grows out at a 90° angle, which does not occur in any *Zelkova serrata.* After this time period it exhibits relatively normal growth pattern as compared to the *Zelkova serrata,* except that it has a fuller canopy, and its limbs do not grow as upright as the *Zelkova serrata.*

SUMMARY OF THE INVENTION

The following characteristics in combination distinguish the new tree named 'JSC Kingsthree' cultivar from other cultivars of *Zelkova serrata.*

1. The 'JSC Kingsthree' cultivar has a distinctive and unique leaf color, shape, and texture, as well as a weeping limb structure that *Zelkova serrata,* and other cultivars of *Zelkova serrata* do not have. The colors of the leaves change throughout the growing season. When the leaves first emerge from their apical meristems, they are reddish-brown (RHS #171A). They quickly become light green for 2 to 3 weeks, turning dark green as they mature. Upper side of young leaves (three-week-old leaves) is dark green (RHS #137A); the upper side of the most mature leaves color is dark green (RHS #136A). The color of the lower side of the immature leaf is a light green (RHS #141D), but changes in the most mature leaves to a darker green (RHS #144A). During fall, the margin of the leaf becomes reddish-brown (RHS #171A) and the leaf along the main vein changes from a light yellow brown (RHS # 163B) to a reddish-brown (RHS #171A).

2. With the distinctive, weeping characteristics, as well as a varying leaf color, shape, and texture, the 'JSC Kingsthree' cultivar will be a popular tree for landscaping applications.

3. The 'JSC Kingsthree' cultivar is cold tolerant. It has withstood very low 20° F. temperatures in late April, long after the leaf buds opened. Most trees in Middle Tennessee were severely damaged during this cold spell that occurred so late in the spring (2007).

4. The 'JSC Kingsthree' cultivar is able to endure drastic changes in moisture levels. There is usually heavy rainfall in the spring and very little rain in July and August in Middle Tennessee (climate Zone 6b, USDA Plant Hardiness Zone Map). However in 2007 there was little rain in the spring and late summer, and the cultivar thrived. Furthermore, throughout the summer 2007, many days reached and broke the record high temperatures for that given day.

5. The 'JSC Kingsthree' cultivar grows moderately. The seedlings grew 3 to 4 feet (or 92 to 122 cm) during their first year and 5 to 6 feet (or 152 to 183 cm) during their second year. During their fourth year, their average trunk diameter measured approximately 2.5 inches (or 6.35 cm).

6. After 4 years of growth, the 'JSC Kingsthree' cultivar has remained insect and pathogen resistant, growing in the fields of the nursery of James D. Cavett at 74 S & W Lane, Estill Springs, Tenn. 37330.

7. The "JSC Kingsthree" cultivar has not been observed under all conditions, and it is not known how the cultivar might respond to various conditions.

BRIEF DESCRIPTION OF THE DRAWINGS

The first photograph (FIG. 1) shows the originally discovered 'JSC Kingsthree' as it looked in 2008, four years after the cultivar's discovery at 74 S&W Lane, Estill Springs, Tenn. 37330. This tree was 4 years old at the time of photography. Notice that the terminal end of the branches bend (or weep) at 30- to 60-degree angles.

The second photograph (FIG. 2) is a closer view of the terminal branches and shows the characteristic 30- to 60-degree bend or droop of the branches that contribute to the weeping appearance of the 'JSC Kingsthree' cultivar. This is the same tree as the one described in FIG. 1, just at a different focus, thus the tree is 4 years old at the time of photography.

Figure 1:
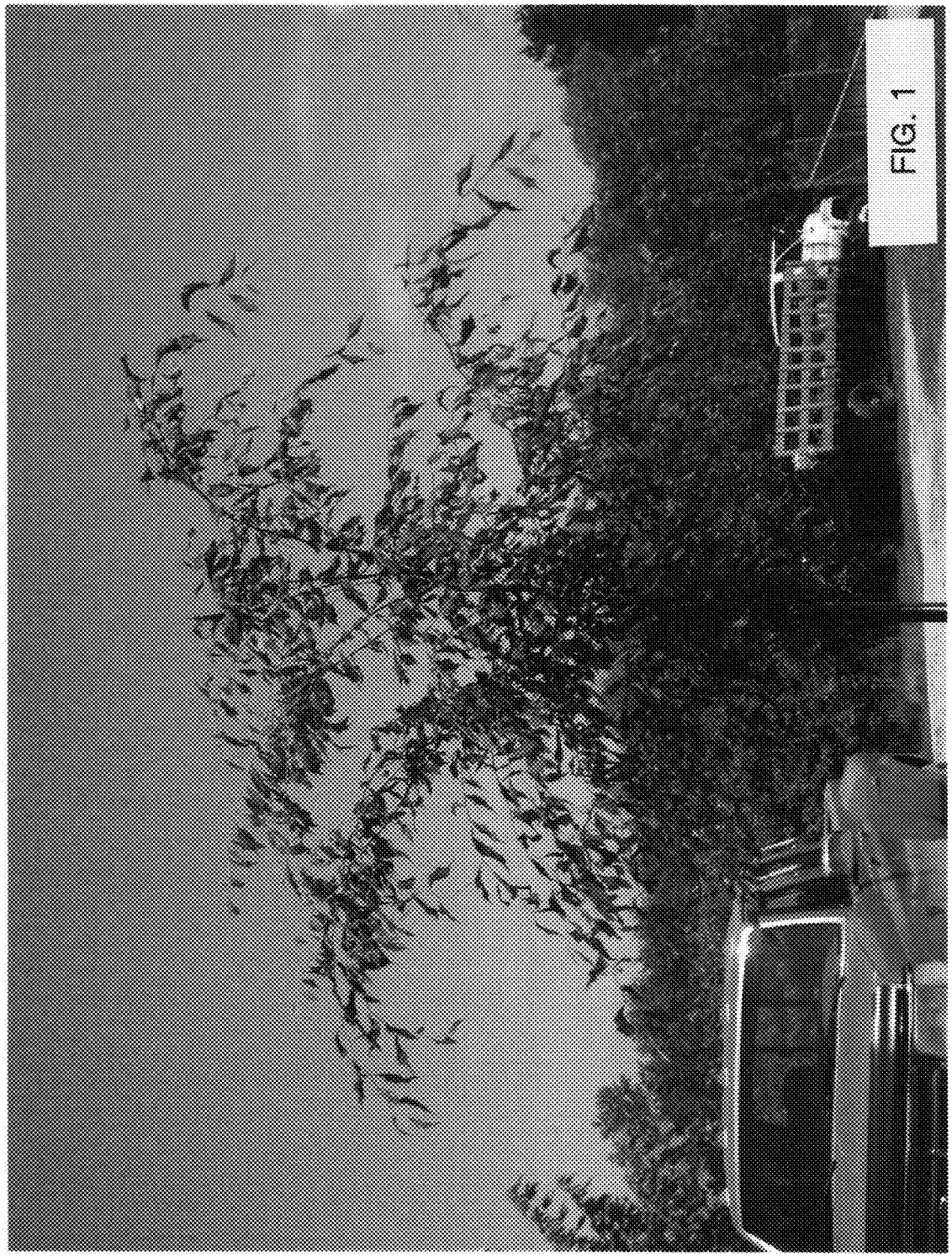
Figure 2:
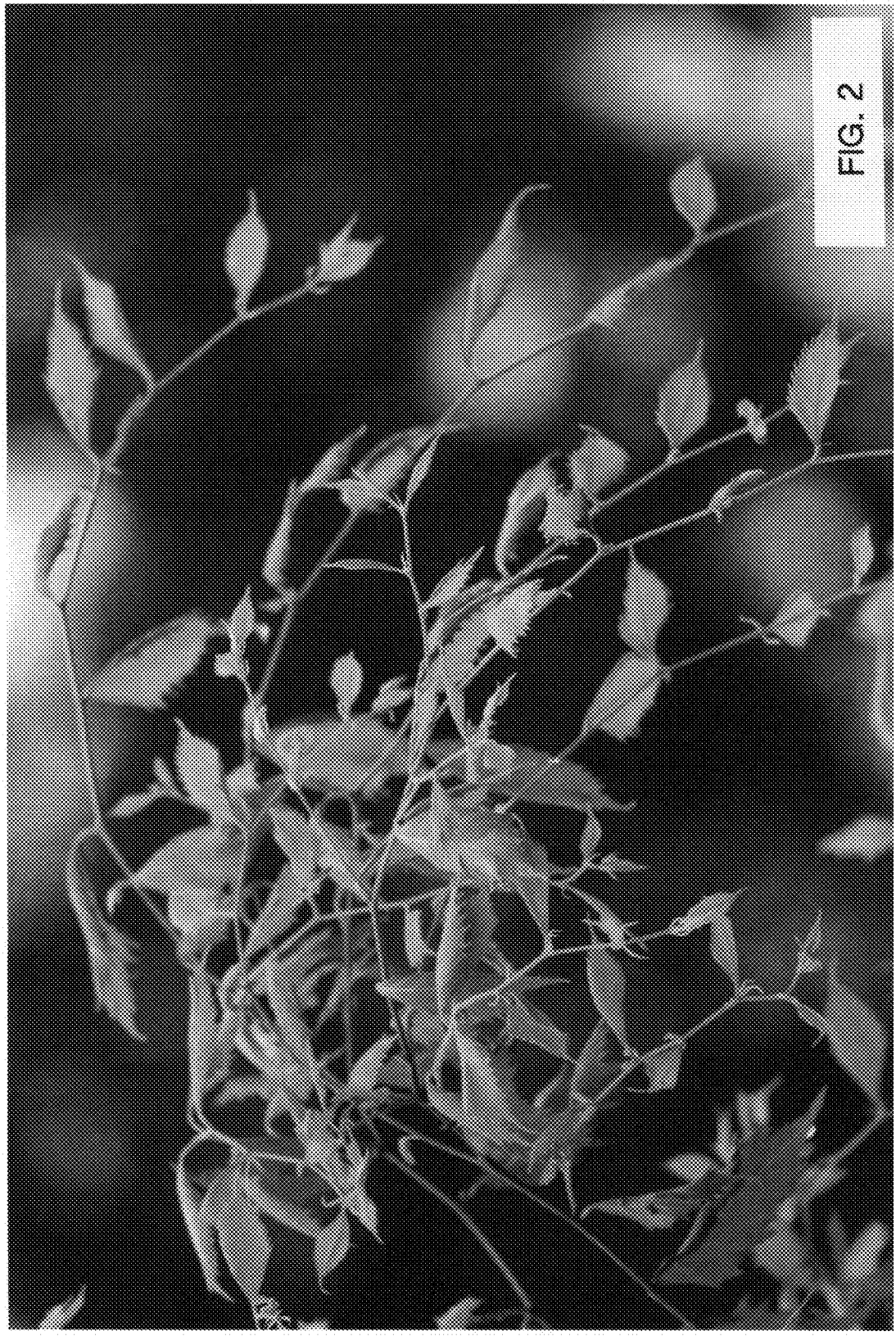
Figure 3:
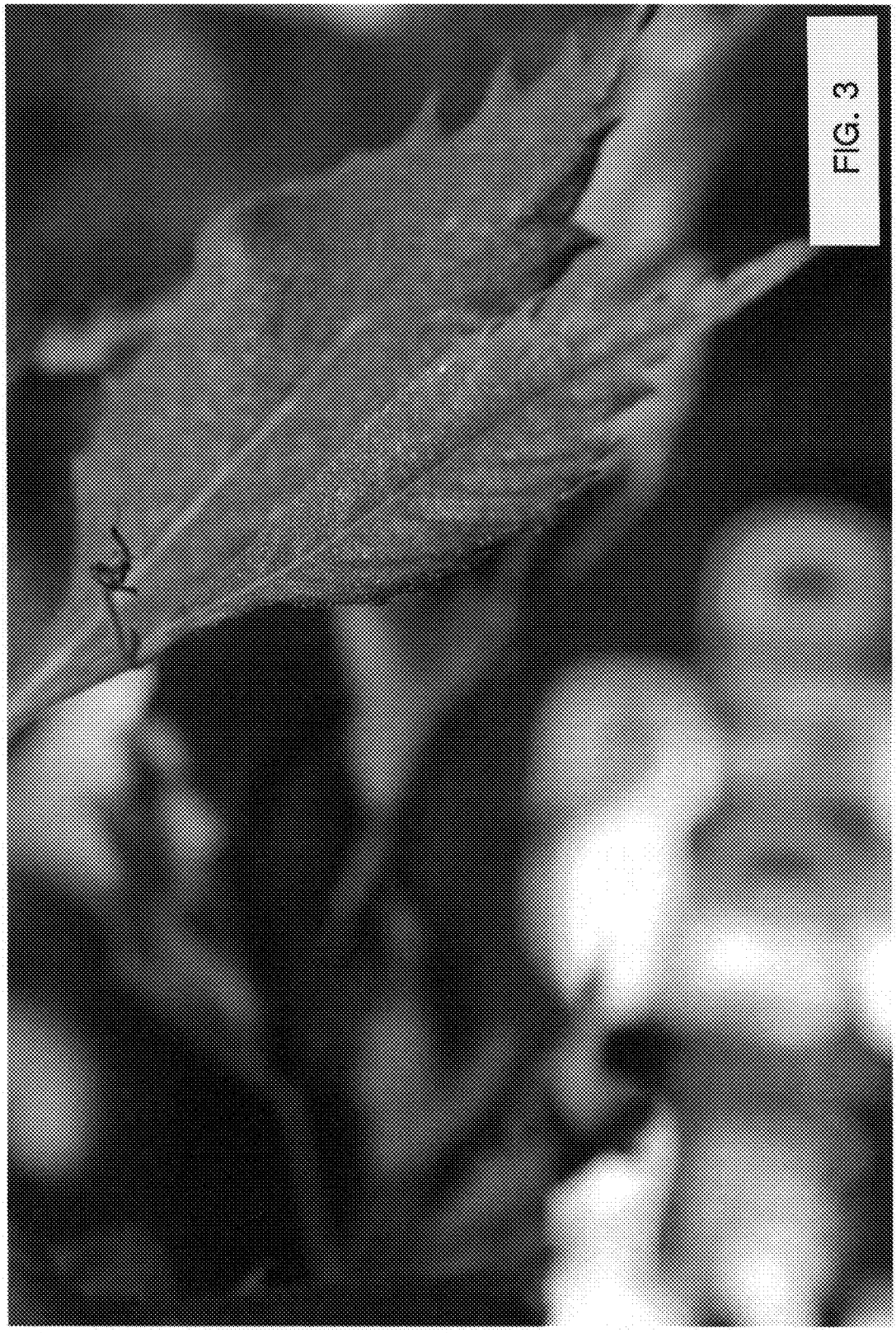

The third photograph (FIG. 3) shows a closer view of the leaf color a couple of weeks after the leaf emerges from its bud. Several of the younger leaves exhibit the characteristic reddish-brown, which then turn green. In comparison there are also mature leaves in this picture that exhibit their dark green color when mature. The tree represented in FIG. 3 was 3 years old at the time of photography.

Figure 4:
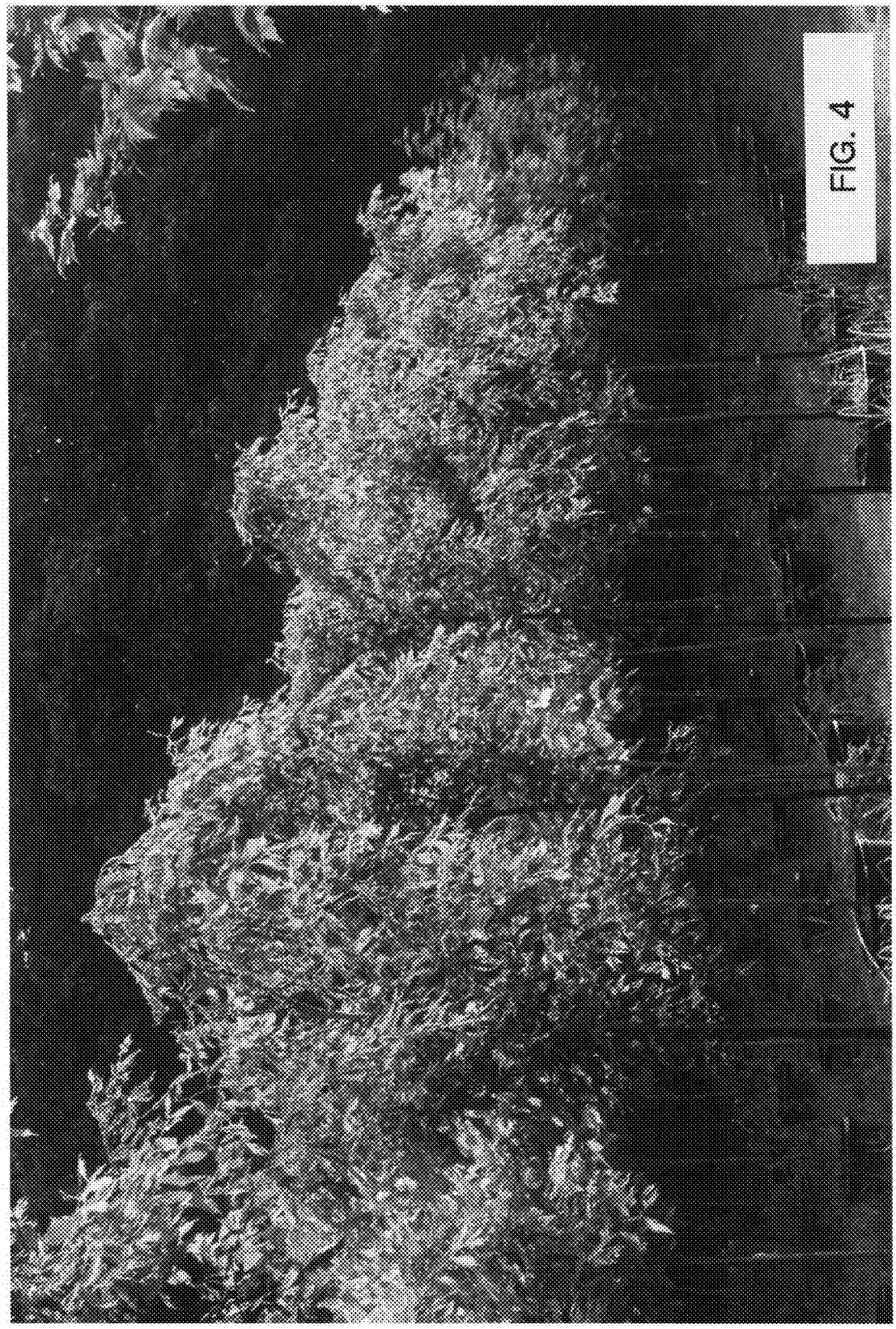

In the fourth photograph (FIG. 4), the trees appear to be covered in a light frost. This frost-like appearance is observed in the early morning or late afternoon when the sun is low in the sky and results from the passage of the sunlight through the trichomes found on the leaf petioles (see FIG. 5). These trees were 3 years old at the time of photography.

Figure 5:
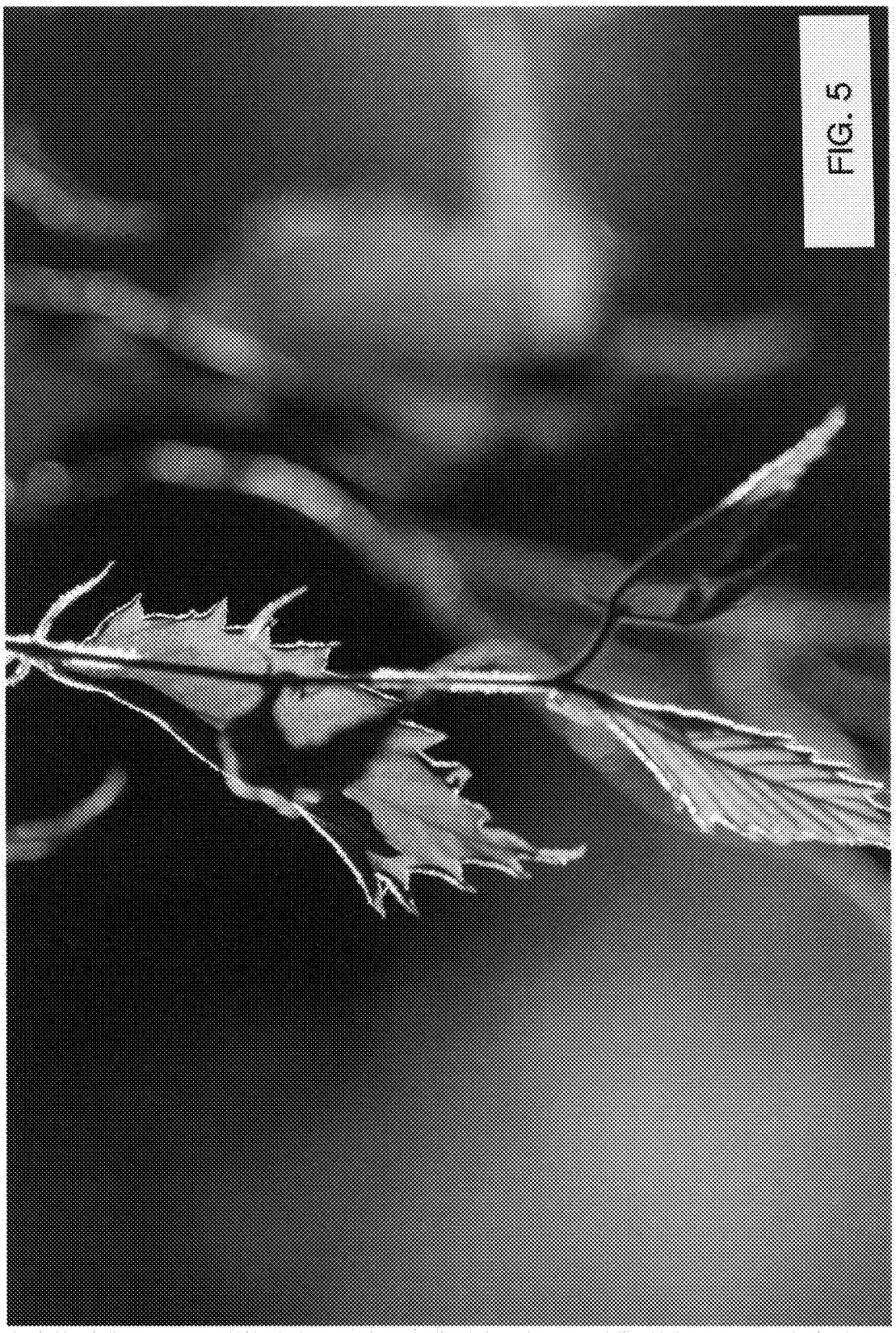

FIG. 5 shows the pubescent appearance of the leaf petiole due to the large number of trichomes found on the petiole surface. The tree represented in FIG. 5 was 3 years old at the time of photography.

Figure 6:
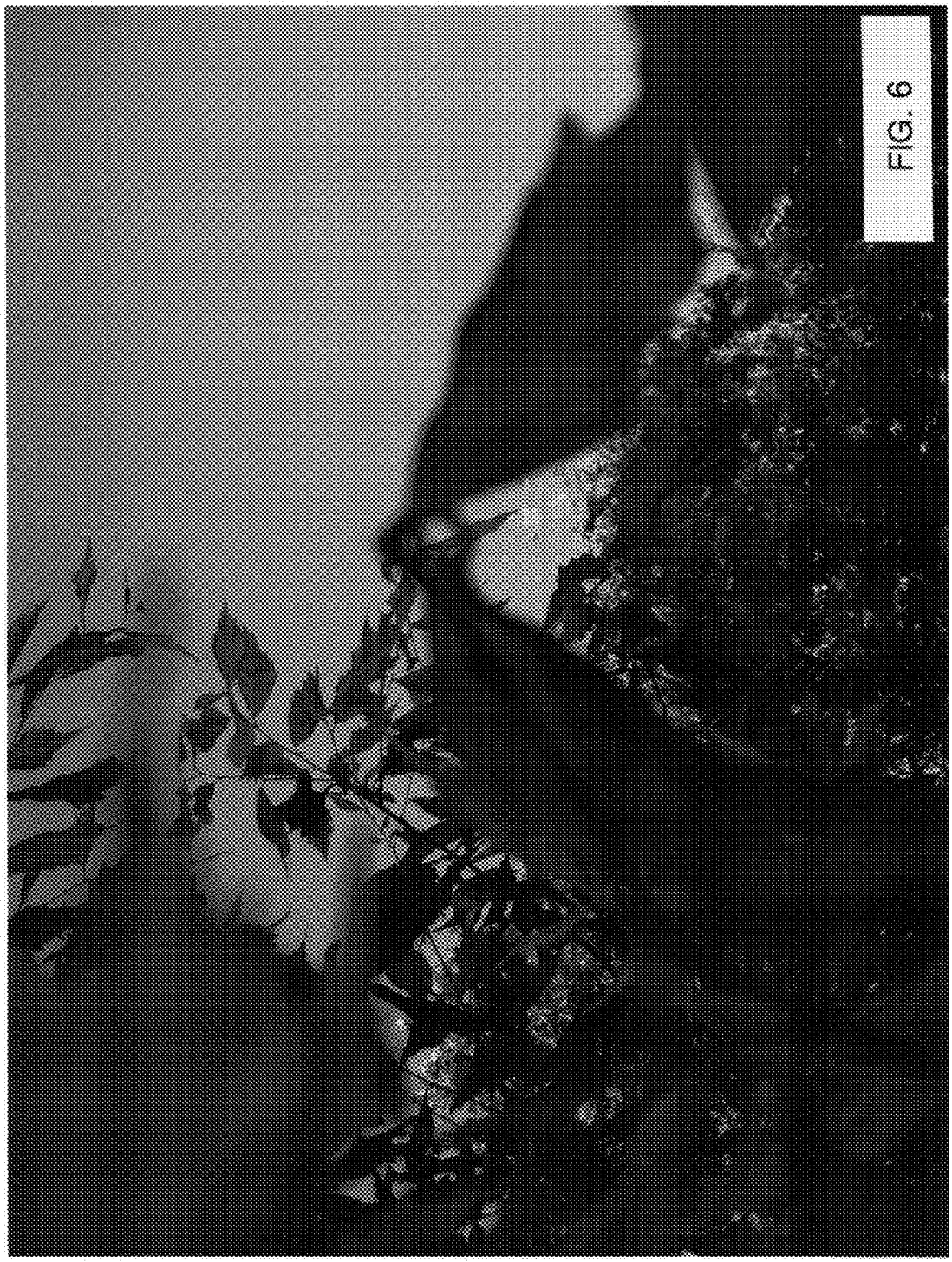

In FIG. 6, we see another characteristic that the 'JSC Kingsthree' cultivar exhibits, which is unique to this cultivar. Occasionally, at the axis of a leaf bud of some branches, the branch grows at a 90-degree angle (or right angle) from the proceeding portion of the branch. This characteristic does not occur on every branch, but does occur in addition to the 30- to 60-degree bend or droop that is observed on every branch, and it contributes to the weeping growth pattern of the 'JSC Kingsthree' cultivar. The tree represented in FIG. 6 was 3 years old at the time of photography.

Figure 7:
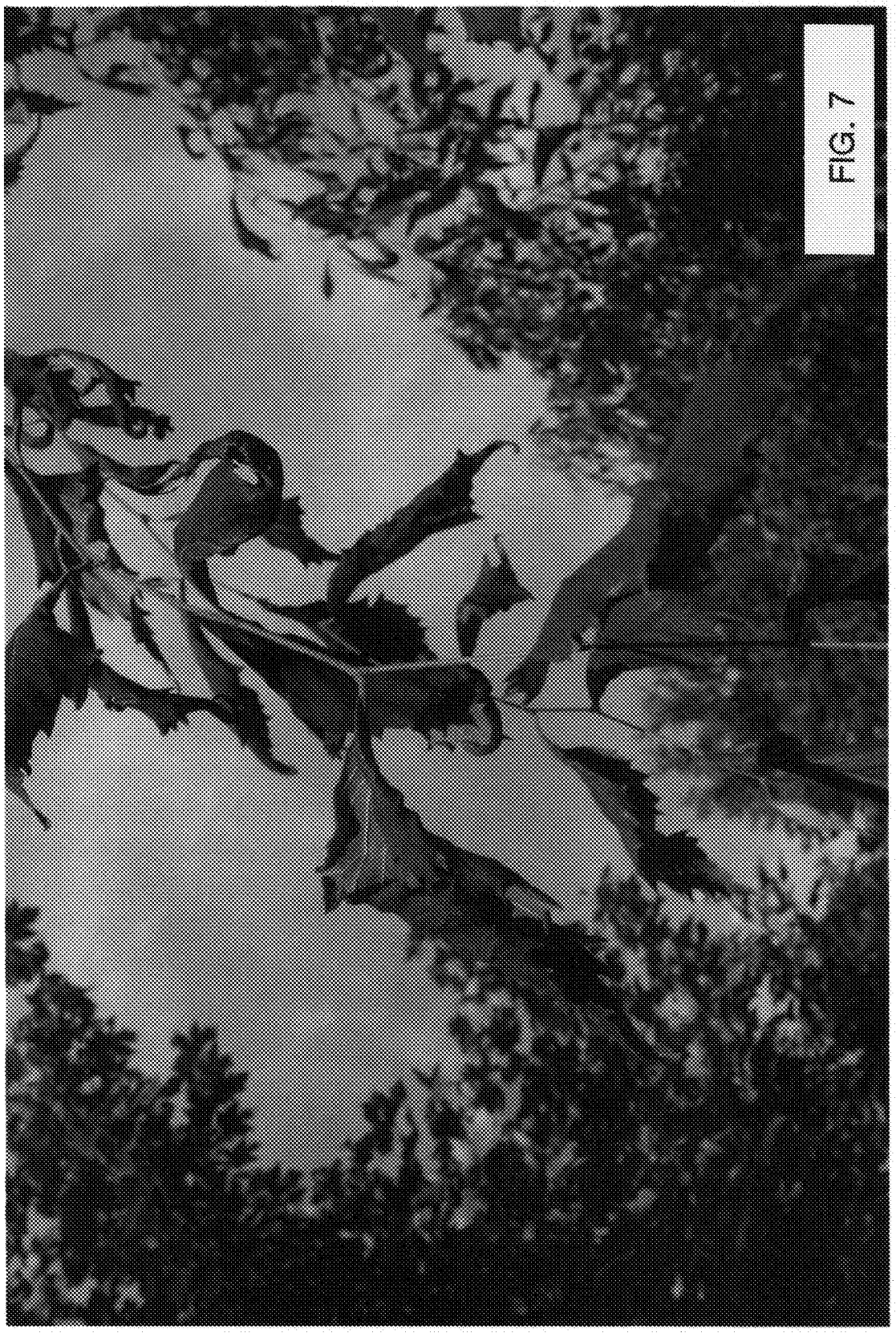

FIG. 7 shows the unique curl that many of the leaves exhibit. The curl follows the main vein of the leaf and begins at the base of the leaf and continues to its apex. The tree represented in FIG. 7 was 3 years old at the time of photography.

Figure 8:
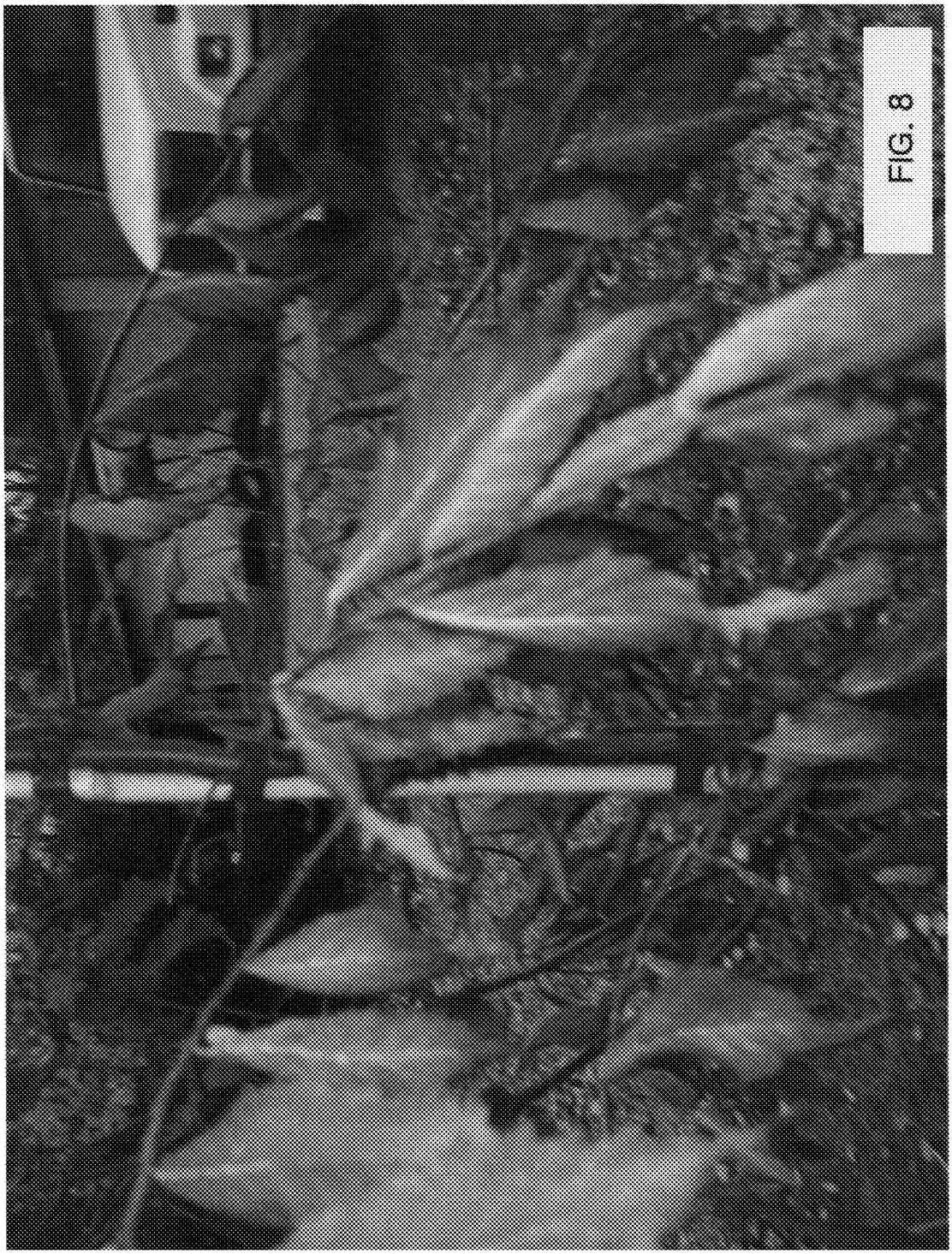

FIG. 8 is a photograph of fall foliage color. The margins of the leaf become red while the leaf along the main vein turns from its summer green color to a light yellow-brown color. The tree represented in FIG. 8 was 4 years old at the time of photography.

DETAILED BOTANICAL DESCRIPTION

The following observations, measurements, and values describe plants grown at 74 S&W Lane, Estill Springs, Tenn. 37330. The actual appearance and characteristics of any individual plan will vary due to horticultural practices and local conditions. The tree used for description is 4 years old. Color references are made to The Royal Horticultural Society Colour Chart except where terms of ordinary significance are used.

Botanical classification: *Zelkova* serrata.

Commercial classification: 'JSC Kingsthree' *zelkova*

Origin: The origin is one specific seedling that had different leaf shape, texture, fall color, branch structure, and growth pattern. Four buds were taken from this one specific seedling and grafted onto four *Zelkova serrata* seedlings. The buds that were grafted onto *Zelkova serrata* were buds taken from the only seedling in the block of *Zelkova serrata* that exhibited these distinct characteristics.

Parentage: A specific seedling found in a block of *Zelkova serrata.*

Propagation: Asexual by softwood cuttings and grafts.

Plant:

*Growth rate.*—Moderate; an average of 3 to 4 feet (or 92 to 120 cm) per year.

*Form.*—Oval.

*Shape.*—Oval to round.

*Height.*—Average size of the 'JSC Kingsthree' is 20 to 26 feet (or 610 to 800 cm). When the observation was taken, the specimen observed was 4 years old.

*Spread.*—Average size of the 'JSC Kingsthree' is 15 to 18 feet (460 to 550 cm). When the observation was taken, the specimen observed was 4 years old.

*Density.*—Thick with foliage.

*Trunk size.*—The diameter at the base of the trunk at ground level of the typical 4-year-old tree is 2.5 inches (or 6.35 cm).

*Bark.*—(Trunk): smooth. The color of the bark on the trunk of a four-year-old tree is predominately greenish-brown (RHS #N199C) with small, discrete bands of gray (RHS #N202C) that circle the trunk and increase in size as the tree matures. Small, raised lenticels are present and is round in shape.

*Branching arrangement.*—Alternate. Angle of attachment: Ranges from 30 to 60 degrees with 60 degrees being most prevalent. Internodal length: Mature branches range from 1.1 inches to 1.4 inches (or 2.8 to 3.6 cm) on a three year-old seedling. The average length of a typical branch is 76.5 inches (or 194 cm) on a 3-year-old tree. Furthermore, at the axis of a leaf bud on some branches, the branch grows at a 90-degree angle (or right angle) from the proceeding portion of the branch.

*Stem.*—The color of mature stems is a reddish-brown (RHS #171A) on the 1-year-old seedling. Typical observed length is up to 3.5 inches (or 9.0 cm) with a diameter from 0.15 to 0.2 inches (or 0.4 to 0.5 cm). On the new growth, the stem color is a mixture of two colors; the youngest portion of the stem is generally red (RHS #44A) and the older portion of the stem is reddish-brown (RHS #171A). The arrangement of leaves on the stem is alternate. The length of new growth on the stem of a five-year-old seedling averages 22 inches (or 55.9 cm) with a diameter of 0.3 to 0.5 cm. The internodal length on the 5-year-old plant varies from 0.15 to 0.4 inches (0.4 cm to 1.0 cm) and average 0.4 inches (1.0 cm).

*Lenticels.*—Small, but conspicuous, light silver to gray in color. They are 5 to 7 mm in length and 0.5 to 1.0 mm in width with an oval shape. The color of the lenticels is silver to gray (RHS #N200C).

*Leaves.*—Deciduous.

*Leaf length.*—Petioles vary from 0.2 inches to 0.3 inches (or 0.5 to 0.8 cm) on young leaves, but average 0.25 inches (or 0.65 cm). Mature leaf length varies from 2.8 to 4.3 inches (7.1 to 10.9 cm) in length and is 1.3 to 2.0 inches (3.3 to 5.1 cm) in width.

*Average leaf width.*—1.2 inches (or 3 cm) on growing branch tips (near the apical meristem) and ~1.5 inches (or 3.8 cm) at the base of the branch.

*Leaf shape.*—Lanceolate.

*Leaf margin.*—Serrated.

*Leaf texture.*—Small hairs (trichomes) are present on the upper and lower epidermis of the leaf, with easily felt veins.

*Leaf quantity.*—Abundant.

*Leaf color.*—When the leaves first emerge from their apical meristems, they are reddish-brown (RHS #171A). They quickly become light green for 2 to 3 weeks, turning dark green as they mature. Upper side of young leaves (three-week-old leaves) is (RHS #137A); the upper side of the most mature leaves color is dark green (RHS #136A). The color of the lower side of the immature leaf is a light green (RHS #141D), but changes in the most mature leaves to a darker green (RHS #144A). The color of the petiole is light green (RHS 146C) when the leaf first emerges from the bud but as it matures it becomes a different shade of yellow-green (RHS 145A) in color. During fall, the margin of the leaf becomes reddish-brown (RHS #171A) and the leaf along the main vein changes from a light yellow brown (RHS # 163B) to a reddish-brown (RHS #171A).

*Leaf ribs and veins.*—The upper rib surface at the petiole end of the leaf is yellow-green (RHS #145B). The lower rib surface (leaf underside) color is light green (RHS #151D). Venation is netted.

*Vegetative buds.*—Terminal bud or apical bud is purple-red (RHS #185B). Lateral buds are conical and 0.10 to 0.14 inches (0.25 to 0.35 cm) in length and reddish-brown in color (RHS #171A).

*Leaf apex.*—The leaf apex is acute.

*Base descriptor.*—Rounded.

Flowers: Has not produced any flowers to date, nor is it believed that it will produce flowers in the future.

Disease and pest resistance: No known susceptibility to diseases or pests common to *Zelkova serrata*.

I claim:

1. A new and distinct cultivar of *Zelkova serrata* tree named 'JSC Kingsthree' as illustrated and described herein.

* * * * *